(12) United States Patent
Tuval

(10) Patent No.: US 10,398,546 B2
(45) Date of Patent: *Sep. 3, 2019

(54) MITRAL PROSTHESIS AND METHODS FOR IMPLANTATION

(71) Applicant: Medtronic Ventor Technologies Ltd., Minneapolis, MN (US)

(72) Inventor: Yossi Tuval, Netanya (IL)

(73) Assignee: MEDTRONIC VENTOR TECHNOLOGIES LTD., Minneapolis, MN (US)

( * ) Notice: Subject to any disclaimer, the term of this patent is extended or adjusted under 35 U.S.C. 154(b) by 57 days.

This patent is subject to a terminal disclaimer.

(21) Appl. No.: 15/348,144

(22) Filed: Nov. 10, 2016

(65) Prior Publication Data

US 2017/0056167 A1 Mar. 2, 2017

Related U.S. Application Data

(63) Continuation of application No. 13/016,866, filed on Jan. 28, 2011, now Pat. No. 9,522,062.

(Continued)

(51) Int. Cl.
*A61F 2/24* (2006.01)
*A61F 2/848* (2013.01)

(52) U.S. Cl.
CPC .......... *A61F 2/2418* (2013.01); *A61F 2/2409* (2013.01); *A61F 2/2412* (2013.01); *A61F 2/2436* (2013.01); *A61F 2/24* (2013.01); *A61F 2002/8483* (2013.01); *A61F 2210/0004* (2013.01); *A61F 2220/0016* (2013.01); *A61F 2220/0075* (2013.01); *A61F 2230/0006* (2013.01); *A61F 2230/0013* (2013.01); *A61F 2230/0069* (2013.01); *A61F 2230/0078* (2013.01); *A61F 2250/006* (2013.01); *A61F 2250/0039* (2013.01)

(58) Field of Classification Search
CPC .. A61F 2/24–2/2418; A61F 2250/0069; A61F 2250/0039; A61F 2/2454
See application file for complete search history.

(56) References Cited

U.S. PATENT DOCUMENTS 5,344,442 A 9/1994 Deac
5,354,330 A 10/1994 Hanson et al.
(Continued)

FOREIGN PATENT DOCUMENTS

CA 2660892 A1 3/2007
CN 101184454 A 5/2008
(Continued)

*Primary Examiner* — Yashita Sharma
*Assistant Examiner* — Rebecca S Preston
(74) *Attorney, Agent, or Firm* — Medler Ferro Woodhouse & Mills PLLC

(57) ABSTRACT

A mitral valve prosthesis and methods for implanting the prosthesis transapically (i.e., through the apex of the heart), transatrially (i.e., through the left atrium of the heart), and transseptally (i.e., through the septum of the heart). The prosthesis generally includes a self-expanding frame and two or more support arms. A valve prosthesis is sutured to the self-expanding frame. Each support arm corresponds to a native mitral valve leaflet. At least one support arm immobilizes the native leaflets, and holds the native leaflets close to the main frame.

13 Claims, 26 Drawing Sheets

Related U.S. Application Data

(60) Provisional application No. 61/307,743, filed on Feb. 24, 2010.

(56) References Cited

U.S. PATENT DOCUMENTS

| | | | |
|---|---|---|---|
| 5,908,451 A | 6/1999 | Yeo | |
| 5,957,949 A | 9/1999 | Leonhardt et al. | |
| 6,296,662 B1 | 10/2001 | Caffey | |
| 6,312,465 B1 | 11/2001 | Griffin et al. | |
| 6,458,153 B1 | 10/2002 | Bailey et al. | |
| 6,558,418 B2 | 5/2003 | Carpentier et al. | |
| 6,730,118 B2 | 5/2004 | Spenser et al. | |
| 7,018,406 B2 | 3/2006 | Seguin et al. | |
| 7,018,408 B2 | 3/2006 | Bailey et al. | |
| 7,137,184 B2 | 11/2006 | Shreck | |
| 9,522,062 B2 * | 12/2016 | Tuval | A61F 2/2418 |
| 2003/0023300 A1 | 1/2003 | Bailey et al. | |
| 2003/0130729 A1 | 7/2003 | Paniagua et al. | |
| 2004/0186563 A1 | 9/2004 | Lobbi | |
| 2004/0236411 A1 | 11/2004 | Sarac et al. | |
| 2004/0260389 A1 | 12/2004 | Case et al. | |
| 2005/0043790 A1 | 2/2005 | Seguin | |
| 2005/0075720 A1 | 4/2005 | Nguyen et al. | |
| 2005/0137688 A1 | 6/2005 | Salahieh et al. | |
| 2005/0137690 A1 | 6/2005 | Salahieh et al. | |
| 2005/0137691 A1 | 6/2005 | Salahieh et al. | |
| 2005/0137692 A1 * | 6/2005 | Haug | A61F 2/2418 623/2.11 |
| 2005/0137695 A1 | 6/2005 | Salahieh et al. | |
| 2005/0143809 A1 | 6/2005 | Salahieh et al. | |
| 2005/0182483 A1 | 8/2005 | Osborne et al. | |
| 2005/0197695 A1 | 9/2005 | Stacchino et al. | |
| 2005/0240200 A1 | 10/2005 | Bergheim | |
| 2006/0025855 A1 | 2/2006 | Lashinski et al. | |
| 2006/0025857 A1 | 2/2006 | Bergheim et al. | |
| 2006/0047338 A1 | 3/2006 | Jenson et al. | |
| 2006/0052867 A1 | 3/2006 | Revuelta et al. | |
| 2006/0058872 A1 | 3/2006 | Salahieh et al. | |
| 2006/0074485 A1 | 4/2006 | Realyvasquez | |
| 2006/0149360 A1 | 7/2006 | Schwammenthal et al. | |
| 2006/0259136 A1 | 11/2006 | Nguyen et al. | |
| 2007/0016286 A1 | 1/2007 | Herrmann et al. | |
| 2008/0071361 A1 | 3/2008 | Tuval et al. | |
| 2008/0071368 A1 | 3/2008 | Tuval et al. | |
| 2008/0140190 A1 | 6/2008 | Macoviak et al. | |
| 2008/0183273 A1 | 7/2008 | Mesana et al. | |
| 2008/0208328 A1 | 8/2008 | Antocci et al. | |
| 2009/0005863 A1 | 1/2009 | Goetz et al. | |
| 2009/0240320 A1 * | 9/2009 | Tuval | A61F 2/2418 623/1.24 |
| 2009/0276040 A1 | 11/2009 | Rowe et al. | |
| 2010/0030330 A1 | 2/2010 | Bobo et al. | |
| 2010/0036479 A1 * | 2/2010 | Hill | A61F 2/2418 623/1.15 |
| 2010/0249918 A1 | 9/2010 | Zhang | |
| 2011/0004296 A1 * | 1/2011 | Lutter | A61F 2/2457 623/1.26 |
| 2011/0137397 A1 | 6/2011 | Chau et al. | |
| 2014/0018906 A1 | 1/2014 | Rafiee | |

FOREIGN PATENT DOCUMENTS

| | | |
|---|---|---|
| WO | 02/22054 A1 | 3/2002 |
| WO | WO03/003943 | 1/2003 |
| WO | 05/002466 | 1/2005 |
| WO | 2005/072654 A1 | 8/2005 |
| WO | 06/070372 | 7/2006 |
| WO | WO2009/033469 | 3/2009 |
| WO | WO2009/094188 | 7/2009 |
| WO | WO2010/008549 | 1/2010 |
| WO | WO2010/098857 | 9/2010 |
| WO | WO2010/099032 | 9/2010 |

* cited by examiner

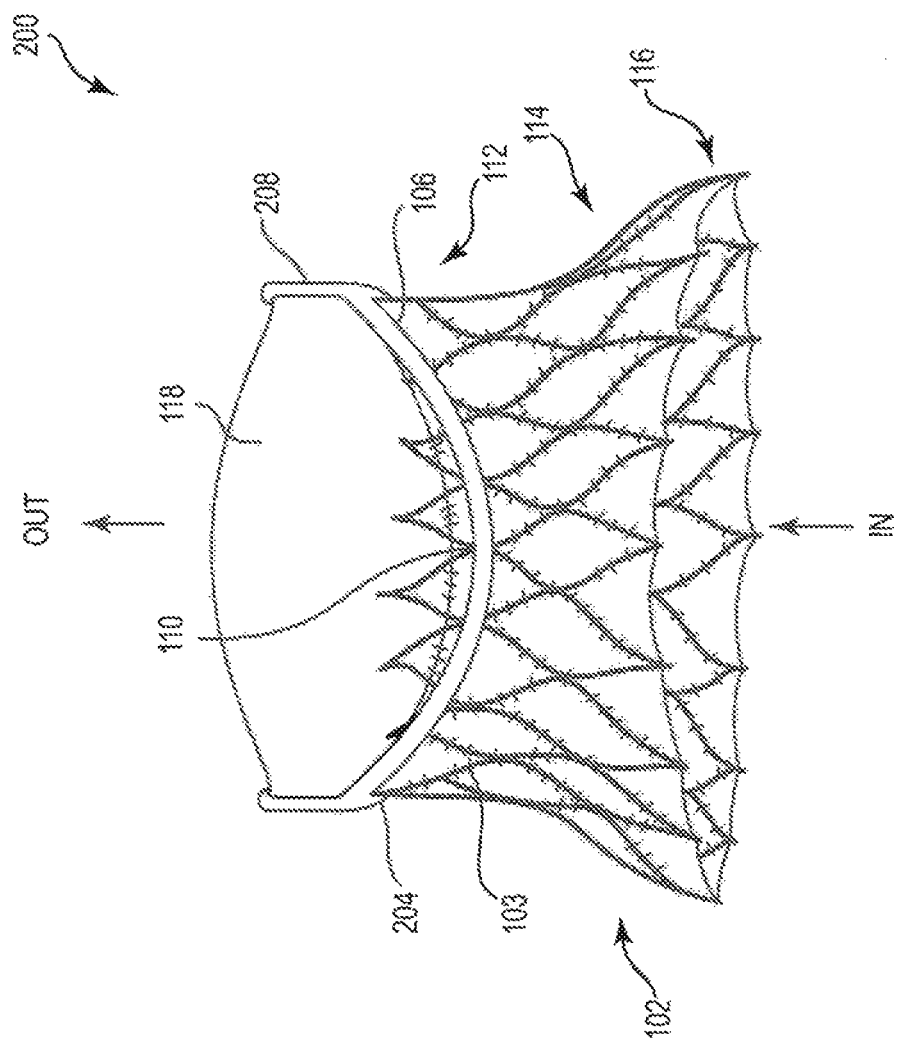

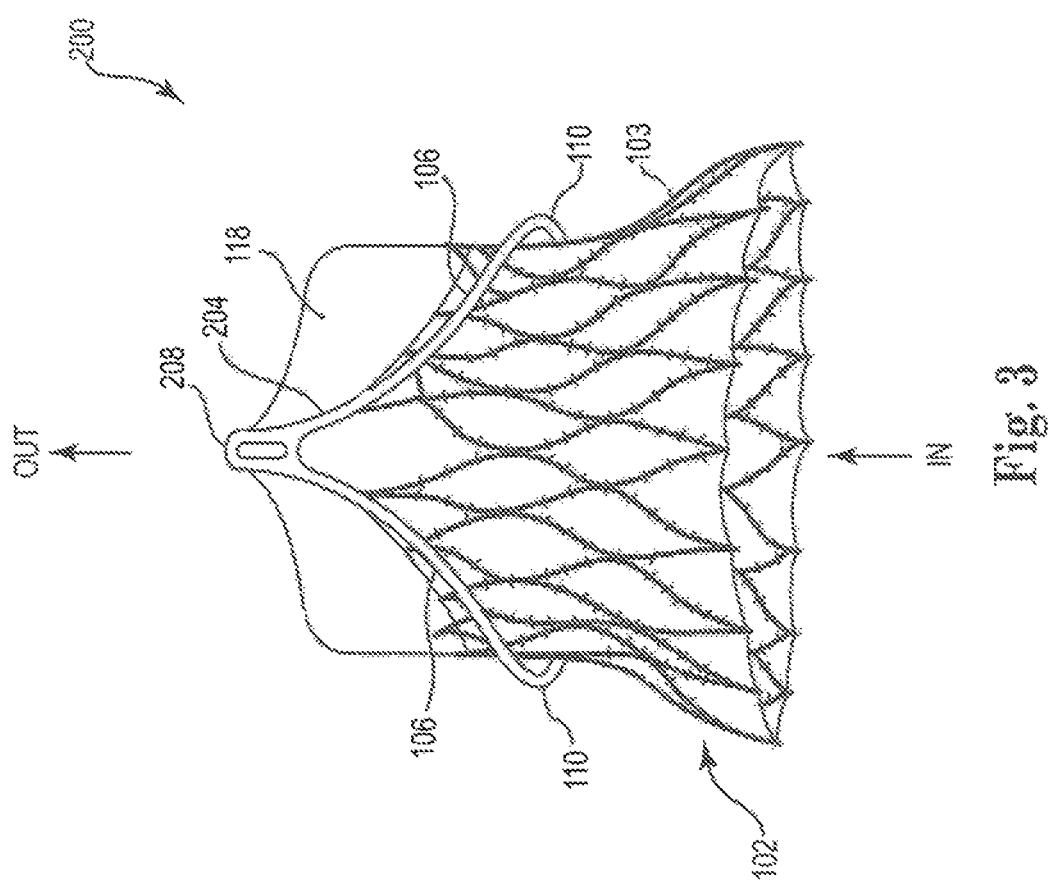

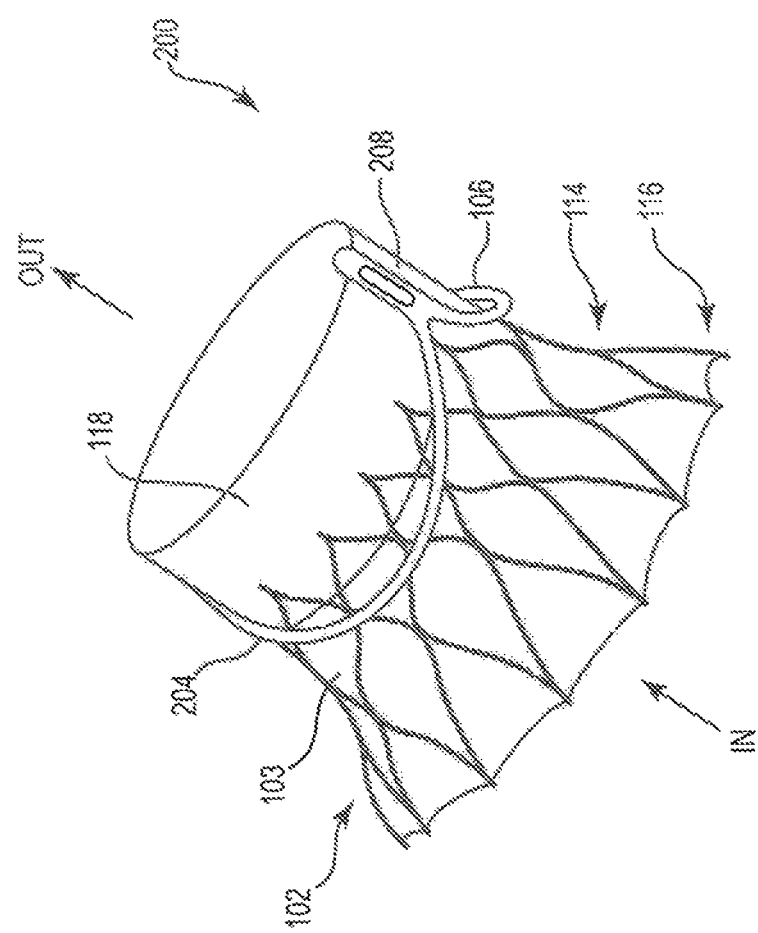

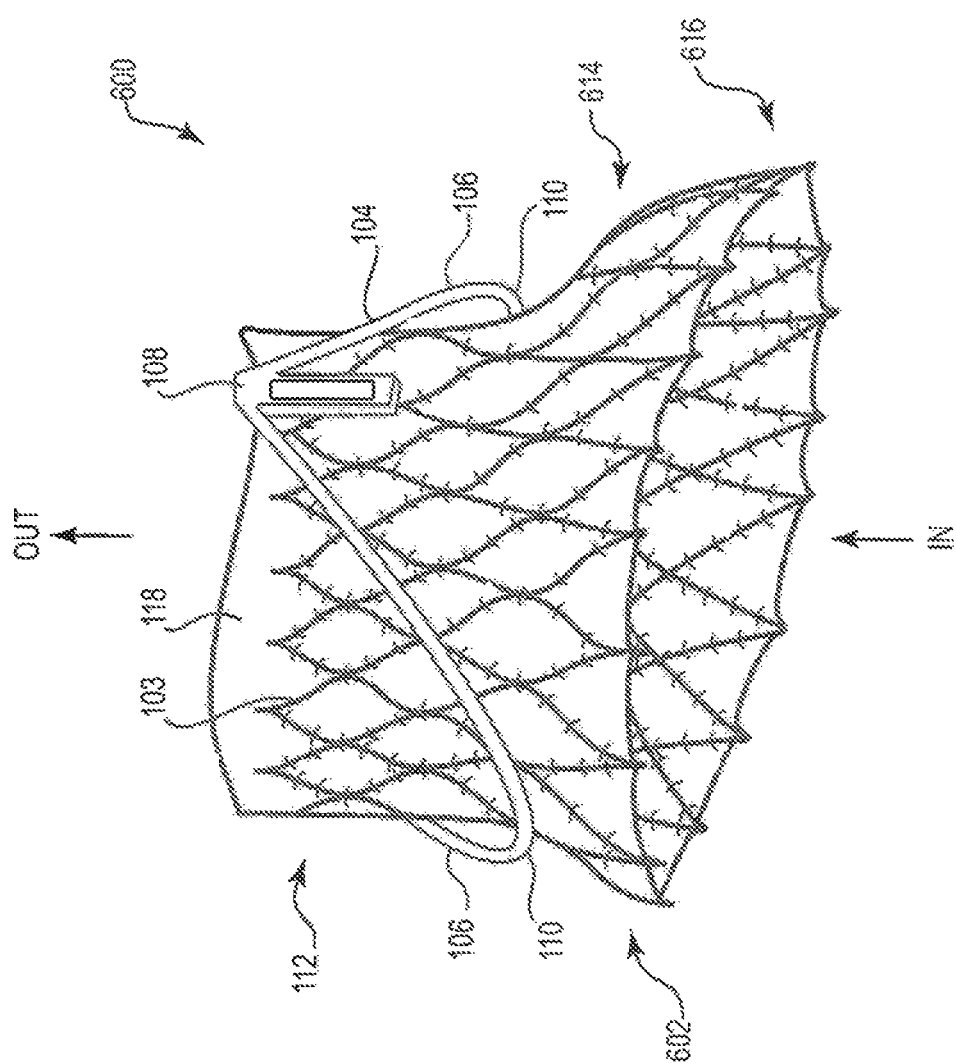

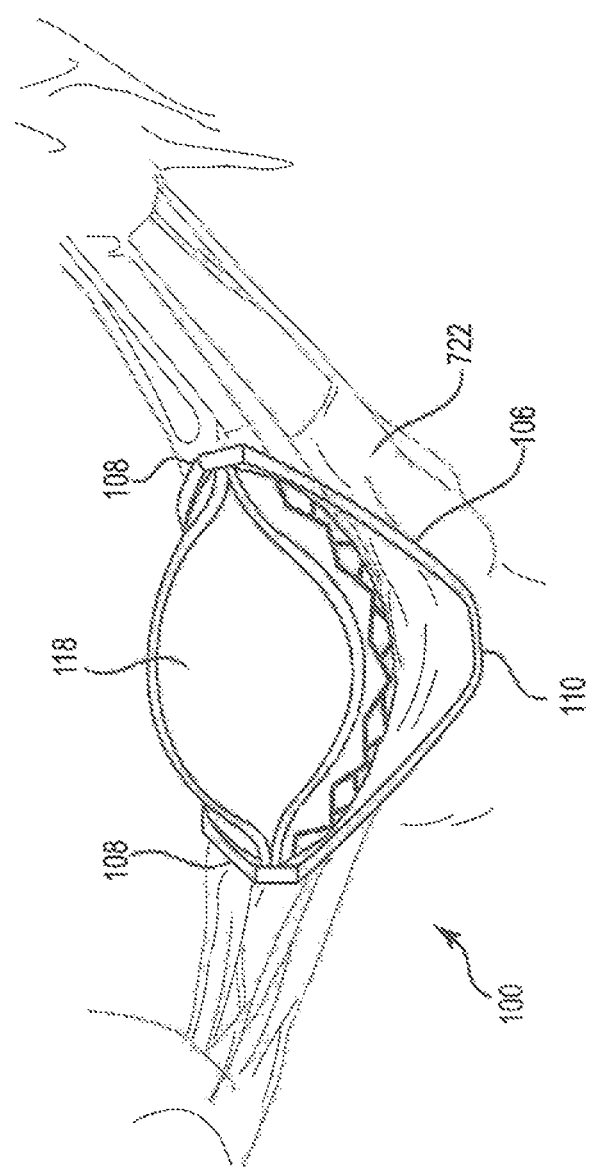

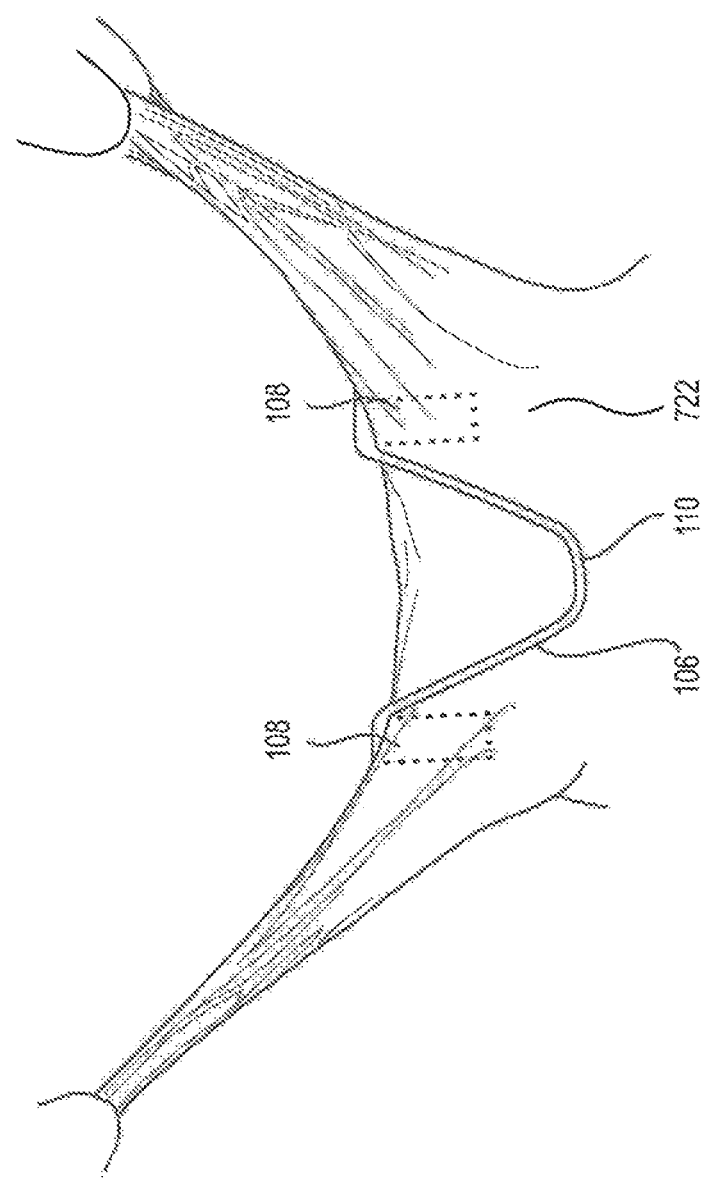

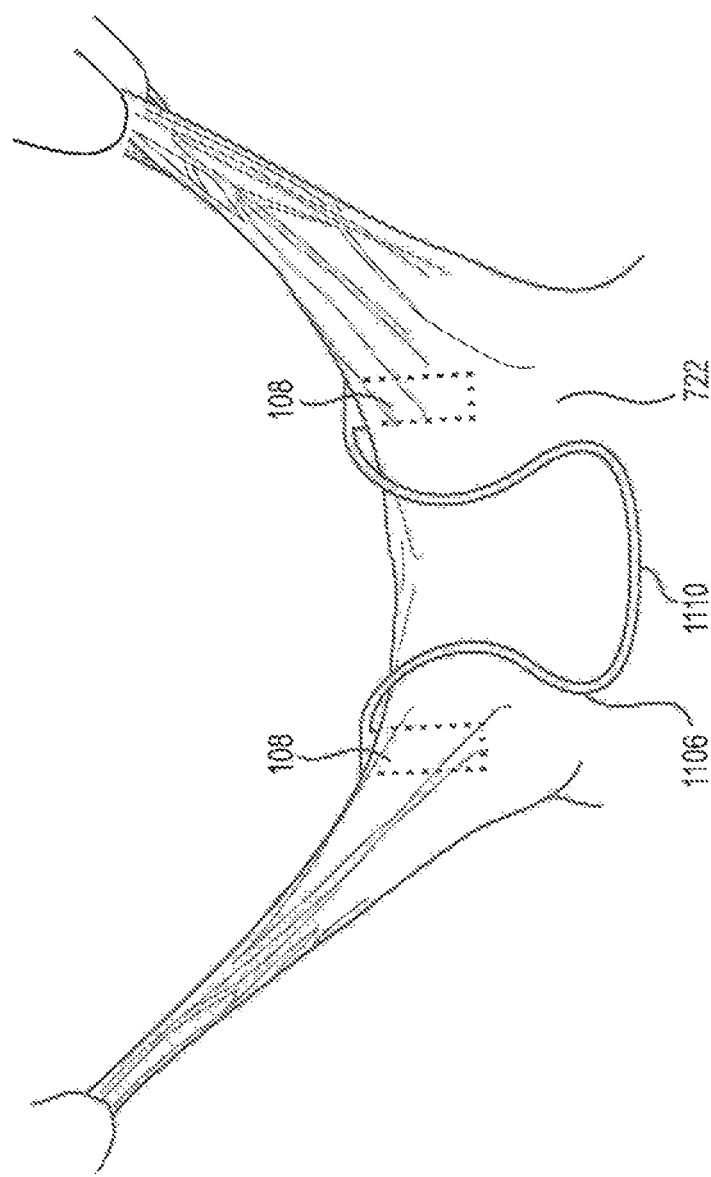

MITRAL PROSTHESIS AND METHODS FOR IMPLANTATION

CROSS REFERENCE TO RELATED APPLICATIONS

This application is a Continuation of and claims the benefit of U.S. patent application Ser. No. 13/016,866, filed Jan. 28, 2011, which claims benefit under 35 U.S.C. 119(e) to U.S. Provisional Patent Application 61/307,743, filed Feb. 24, 2010, the disclosures of which are incorporated by reference herein in their entirety.

BACKGROUND OF THE INVENTION

Field of the Invention

The present invention is related to artificial heart valves. More specifically, the present invention is directed to an artificial mitral valve prosthesis and methods of implanting the prosthesis.

Background Art

The mitral valve exhibits two types of pathologies: regurgitation and stenosis. Regurgitation is the more common of the two defects. Typically, either defect is trailed by ii surgical repair. Under certain condition, however, the mitral valve must be replaced. Standard approaches to mitral valve replacement require cutting open the left side of the heart to access the native mitral valve. Such procedures are traumatic. Further, similar to aortic valve replacement, many patients requiring mitral valve replacement are inoperable or deemed to pose high surgical risk. This problem is lessened by the emerging techniques for minimally invasive mitral valve repair, but still many of those techniques require arresting the heart and funneling the blood through a heart-lung machine. What is needed is a mitral valve prosthesis and method of implantation that minimizes the traumatic impact on the heart while effectively replacing native leaflet function. A consistent, reproducible, and safe method to introduce a prosthesis into the mitral position in a minimally invasive fashion could be attractive for numerous reasons, such as: a) it can treat both functional and degenerative mitral regurgitation (MR); b) it can treat mitral stenosis; c) it can offer a remedy to inoperable patients, high risk surgical patients, and those that cannot tolerate bypass; d) it can allow less proficient surgeons to perform mitral valve procedures; and e) it can enable more consistency in measuring outcome.

The following are herein incorporated by reference in their entirely: U.S. Pat. Nos. 5,354,330; 5,344,442; 5,908,451; 5,957,949; 6,296,662; 6,312,465; 6,458,153; 6,558,418; 6,730,118; 7,018,406; 7,018,408; and 7,137,184; U.S. Patent Application Publication Nos. 2003/0023300; 2003/0130729; 2004/0186563; 2004/0236411; 2004/0260389; 2005/0075720; 2005/0137688; 2005/0137690; 2005/0137691; 2005/0137695; 2005/0143809; 2005/0182483; 2005/0197695; 2005/0240200; 2006/0025857; 2006/0025855; 2006/0047338; 2006/0052867; 2006/0074485; 2006/0259136; 2006/0058872; 2006/0149360; and 2008/0071368; and PCT Publication Nos. WO 05/002466; and WO 06/070372;

BRIEF SUMMARY OF THE INVENTION

Provided herein is a mitral valve prosthesis and methods for implanting the prosthesis transapically (i.e., through the apex of the heart), transatrially (i.e., through the left atrium of the heart), and transseptally (i.e., through the septum of the heart). The prosthesis generally includes a self-expanding frame and two or more support arms. A valve prosthesis is sutured to the self expanding frame. Each support arm corresponds to a native mitral valve leaflet. One or more support arms act to immobilize the native leaflets, and hold the native leaflets close to the frame. Such configuration achieves numerous goals. For example, such configuration can: prevent the native leaflets from obstructing flow through the left ventricular outflow tract (LVOT); prevent the native leaflets from interacting with the prosthetic leaflets; recruit the native leaflets in minimizing peri-valvular leaks; maintain proper alignment of the valve prosthesis; avoid systolic anterior mobility; and maintain valve stability by preventing migration of the valve into the atrium or ventricle. The design of the prosthesis also mimics the native valve and supports a non-round in vivo configuration, which better reflects native valve function.

The prosthesis is generally designed to include two or more commissural posts that are relatively parallel with and level to the ends of the prosthetic valve leaflets, which prevents interaction between the prosthesis and the LVOT and/or native aortic valve. The prosthesis is also generally designed such that diverging commissures are not required because the orifice area is sufficiently large and pressure recovery it not a concern. The inlet end of the prosthesis is wider than the valve segment al the native annular level to prevent migration into the ventricle and to improve sealing of the valve against the atrial wall. The inlet end of the prosthesis may also be designed asymmetrically to accommodate the anterior horn of the atrium, which is associated anatomically with the position of the aortic valve. Fixation barbs at the level of the inlet may provide further fixation to proem device migration into the ventricle.

BRIEF DESCRIPTION OF THE DRAWINGS/FIGURES

The accompanying figures, which are incorporated herein, form part of the specification and illustrate embodiments of a mitral valve prosthesis and methods of implantation. Together with the description, the figures further serve to explain the principles of and to enable a person skilled in the relevant art(s) to make, use, and implant the valve prosthesis described herein. In the drawings, like reference numbers indicate identical or functionally similar elements.

FIG. 2 is a side view of a mitral valve prosthesis, in accordance with an alternative embodiment presented herein.

FIG. 3 is another side view of the mitral valve prosthesis of FIG. 2.

FIG. 5 is another perspective view of the mitral valve prosthesis of FIG. 2.

FIG. 6 is a perspective view of a mitral valve prosthesis, in accordance with an alternative embodiment presented herein.

FIG. 9 is a view of an implanted mitral valve prosthesis, in accordance with one embodiment presented herein.

FIGS. 10A-10D show alternative embodiments of engagement arms for a mitral valve prosthesis.

DETAILED DESCRIPTION OF THE INVENTION

The following detailed description of mitral valve prostheses and methods for implantation refers to the accompanying figures that illustrate exemplary embodiments. Other embodiments are possible. Modifications can be made to the embodiments described herein without departing from the spirit and scope of the present invention. Therefore, the following detailed description is not meant to be limiting.

Figure 1A:
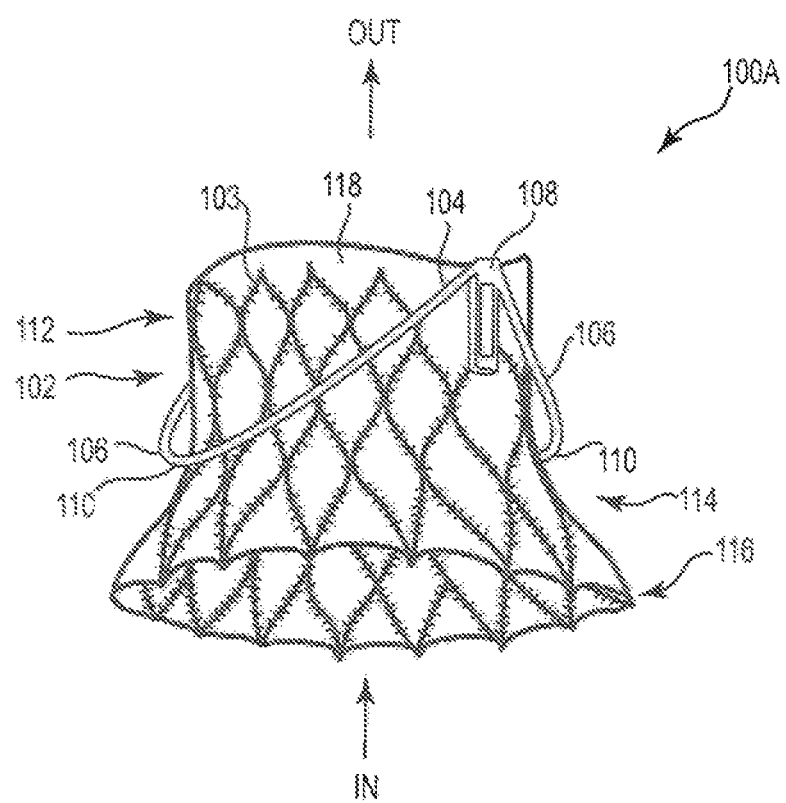
FIG. 1A is a perspective view of a mitral valve prosthesis, in accordance with one embodiment presented herein.

FIG. 1A is a perspective view of a mitral valve prosthesis 100A, in accordance with one embodiment presented herein. Mitral valve prosthesis 100A includes an inner support structure (or main frame) 102 and an outer support structure 104. Outer support structure 104 includes outer engagement arms (or outer support arms) 106. As shown, mitral valve prosthesis 100A includes two outer engagement arms 106 to anatomically match the native mitral valve leaflets. Upon implantation outer engagement arms 106 clamp and immobilize the native mitral valve leaflets, and hold the native leaflet close to inner support structure 102. Each outer engagement arm 106 includes a trough 110 and takes an upward concave structure having ends meeting at junctures, or commissure post 108.

Inner support structure 102 includes a distal section 112, a relatively narrow throat section 114, and a proximal section 116. As used herein the term "distal" is understood to mean downstream in the direction of blood flow. The term "proximal" is intended to mean upstream in the direction of blood flow. Inner support structure 102 includes a generally uniform, circular cross-section along the length of the longitudinal axis of valve prosthesis 100A. As shown, distal section 112, narrow throat section 114, and proximal section 116 include diamond-shaped cells 103. Alternative shapes and configurations of the cells (or struts) 103 may be employed. Distal section 112 can be formed in a straight fashion (i.e., cylindrical and parallel to the longitudinal axis of prosthesis 100A) or in a flared fashion (i.e., diverging away from the longitudinal axis of prosthesis 100A). Proximal section 116 is generally formed to bulge outward from narrow throat section 114, and may be formed straight or flared outward. Proximal section 116 is the blood inlet end of valve prosthesis 100A. Proximal section 116 is generally wider than narrow throat section 114, and is generally wider than the native valve segment at the native annular level. Such a configuration prevents migration of prosthesis 100A into the ventricle and improves sealing of prosthesis 100A against the atrial wall.

Inner support structure 102 is also configured to be expandable (preferably self-expandable), and may be formed of a memory alloy such as NITINOL. Other biocompatible metals may also be used. Outer support structure 104 may also be formed of a memory alloy such as NITINOL, or other biocompatible metals. Inner support structure 102 and outer support structure 104 may be integrally formed, or may comprise separate modular components that are attached to one another. In one embodiment, inner support structure 102 is designed to flex and deform so as to mimic the natural cardiac movements of the heart through the cardiac cycle. In another embodiment, inner support structure 102 is designed in a rigid fashion to avoid flexing or deformation during the cardiac cycle.

Sutured to inner support structure 102 is a prosthetic valve 118. In one embodiment, valve 118 is sewn onto inner support structure 102 as described in U.S. Patent Application Publication No. 2008/0071368, which is incorporated herein, in its entirety, by reference. Valve 118 may be formed of a biocompatible synthetic material, synthetic polymer, an autograft tissue, xenograft tissue, or other alternative materials.

Alternative designs may include three engagement arms, three leaflets, and/or three commissure posts.

Figure 1B:
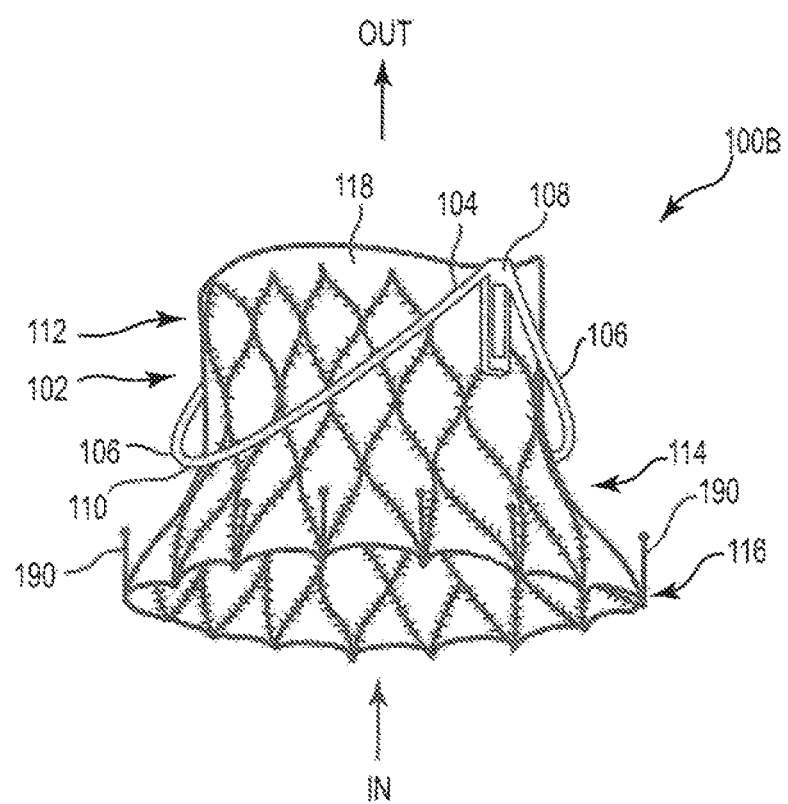
FIG. 1B is a perspective view of a mitral valve prosthesis, in accordance with an alternative embodiment.

FIG. 1B is a perspective view of a mitral valve prosthesis 100B, in accordance with an alternative embodiment. Mitral valve prosthesis 100B differs from prosthesis 100A only in that proximal section 116 includes fixation barbs 190 to provide further fixation support and to prevent migration of prosthesis 100B into the ventricle.

Figure 4:
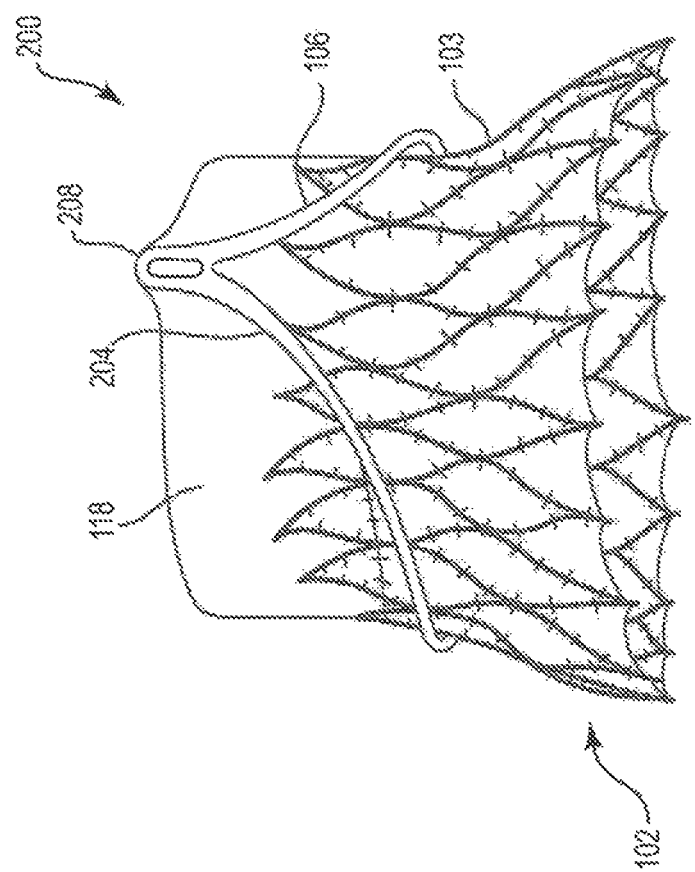
FIG. 4 is a perspective view of the mitral valve prosthesis of FIG. 2.

FIG. 2 is a side view of a mitral valve prosthesis 200, in accordance with an alternative embodiment presented herein. FIG. 3 is another side view of valve prosthesis 200. FIG. 4 is a perspective view of valve prosthesis 200. FIG. 5 is another perspective view of valve prosthesis 200. Similar to mitral valve prosthesis 100A of FIG. 1A, mitral valve prosthesis 200 includes an inner support structure 102 and an outer support structure 204. However, outer support structure 204 differs from the outer support structure 104 of FIG. 1A in that outer support structure 204 includes outer engagement arms 106 that couple to the proximal end of commissure post 208.

As shown in FIG. 3, commissure post 208 extends upward from the ends of engagement arms 106. In this embodiment, commissure posts 208 are parallel to and level with the ends of prosthetic valve leaflets 118. In other words, the distal ends of commissure posts 208 are on plane with the ends of the valve leaflets 118. When valve prosthesis 200 is implanted in the native mitral valve, the commissures of the native mitral valve sit within the vertex formed by the two ends of outer engagement arms 106. As such, valve prosthesis 200 avoids interaction between valve 118 and the LVOT and/or native aortic valve.

FIG. 6 is a perspective view of a mitral valve prosthesis 600A, in accordance with another embodiment presented herein. Similar to mitral valve prosthesis 100A of FIG. 1A, mitral valve prosthesis 600A includes an inner support structure 602 and outer support structure 104. However, the shape of inner support structure 602 differs from the shape of inner support structure 102 of FIG. 1A. Specifically, proximal section 616 of inner support structure 602 is formed asymmetrically to accommodate the anterior horn of the atrium, which is associated anatomically with the position of the aortic valve. Proximal section 616 is generally wider than narrow throat section 614, and is generally wider than the native valve segment at the native annular level. Such a configuration prevents migration of prosthesis 600A into the ventricle and improves sealing of prosthesis 600A against the atrial wall. In one embodiment, narrow throat section 614 may have a circular cross-section, while proximal section 616 has a non-circular cross-section (e.g., oval, asymmetric, etc.). In an alternative embodiment, proximal section 616 may also include fixation barbs 690 (as shown with reference to prosthesis 600B in FIG. 11B) to provide further fixation and to prevent migration of prosthesis 600B into the ventricle. In general, the cross-section of inner support structure 602 is a non-uniform, non-circular shape. As shown, distal section 112, narrow throat section 614, and proximal section 616 include generally diamond-shaped cells. Alternative shapes and configurations of the cells (or struts) may be employed.

Figure 7A:
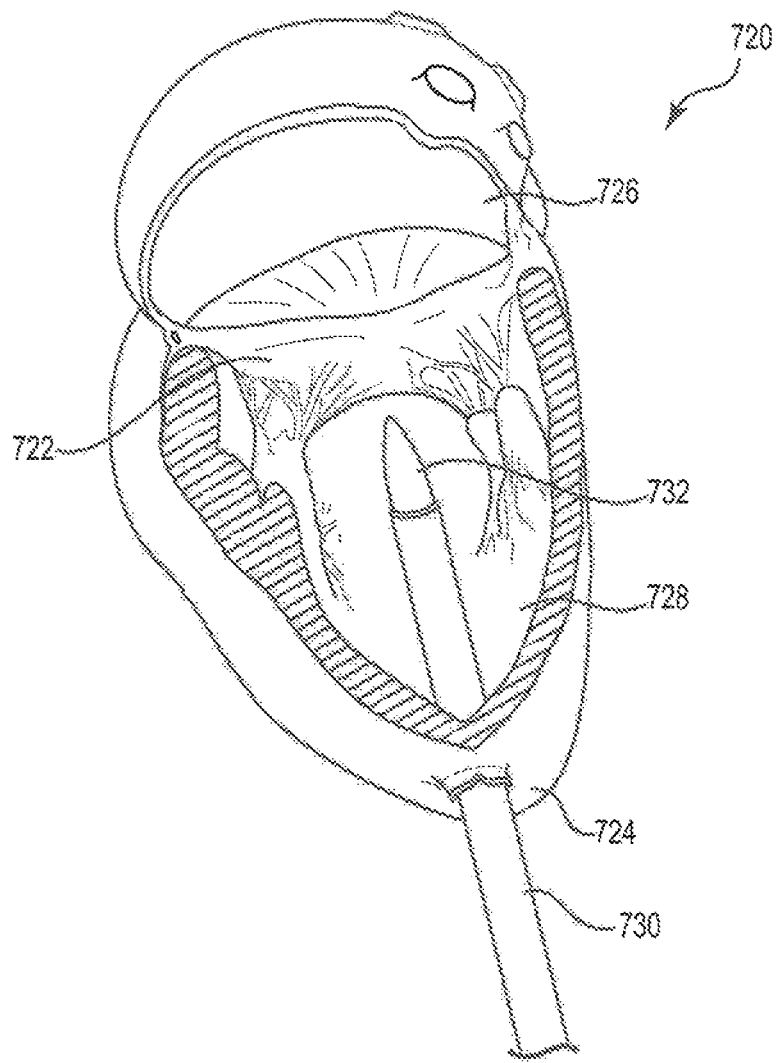
FIGS. 7A-7F depict a method of implanting a mitral valve prosthesis transapically.
Figure 7B:
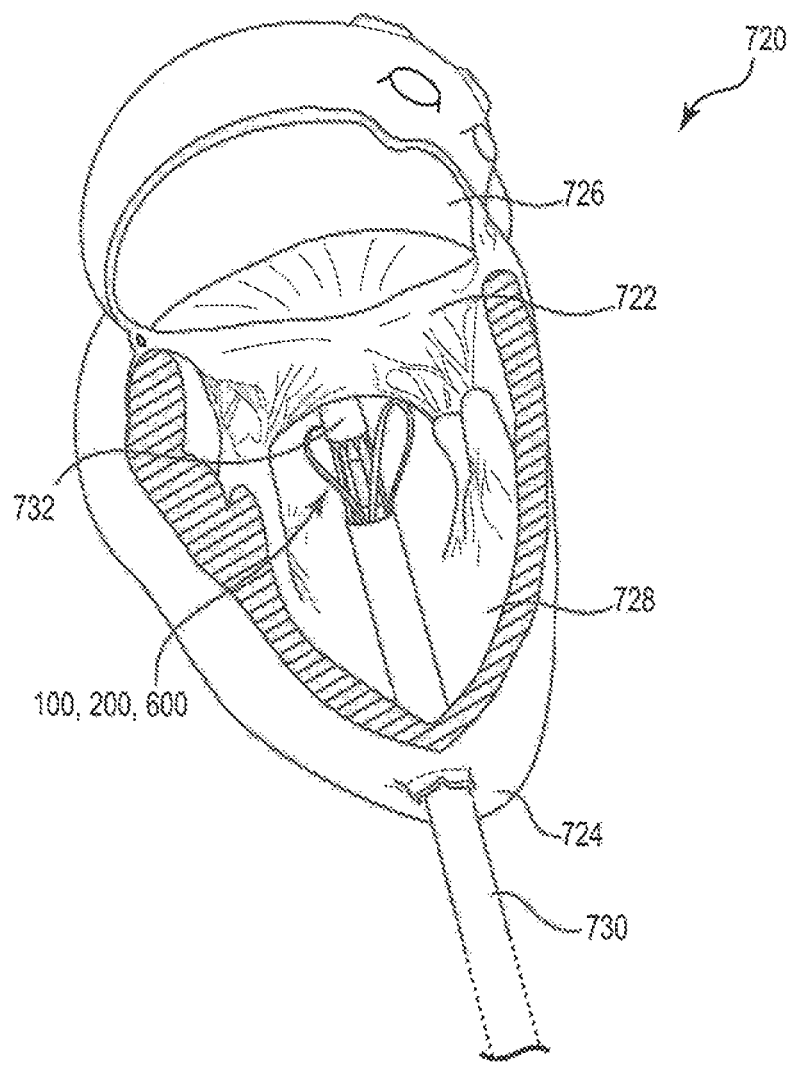
Figure 7C:
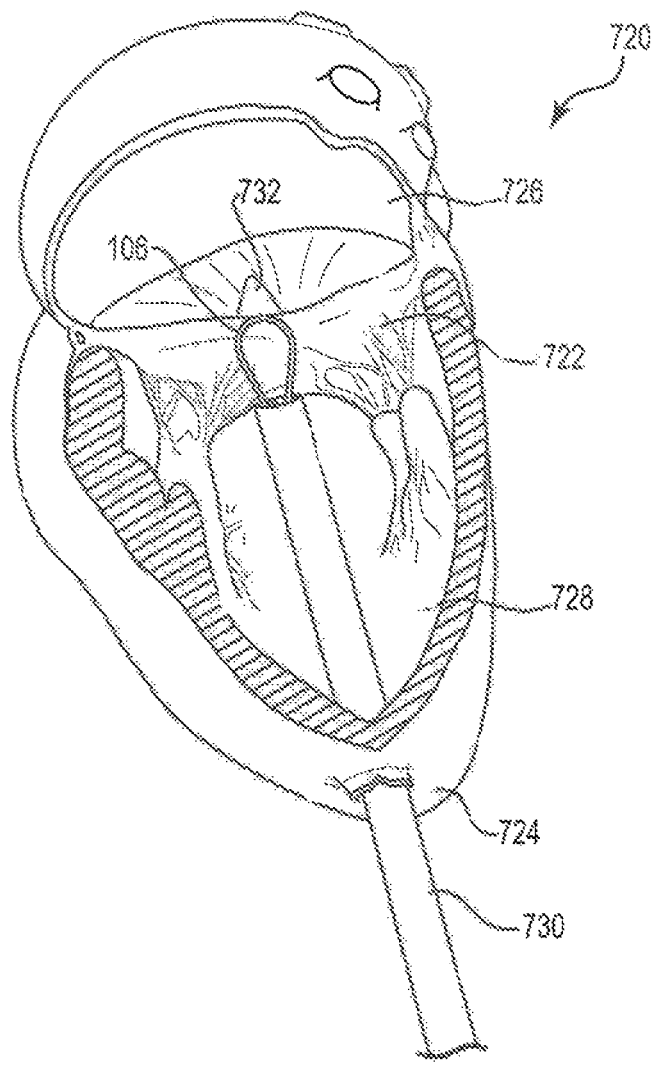
Figure 7D:
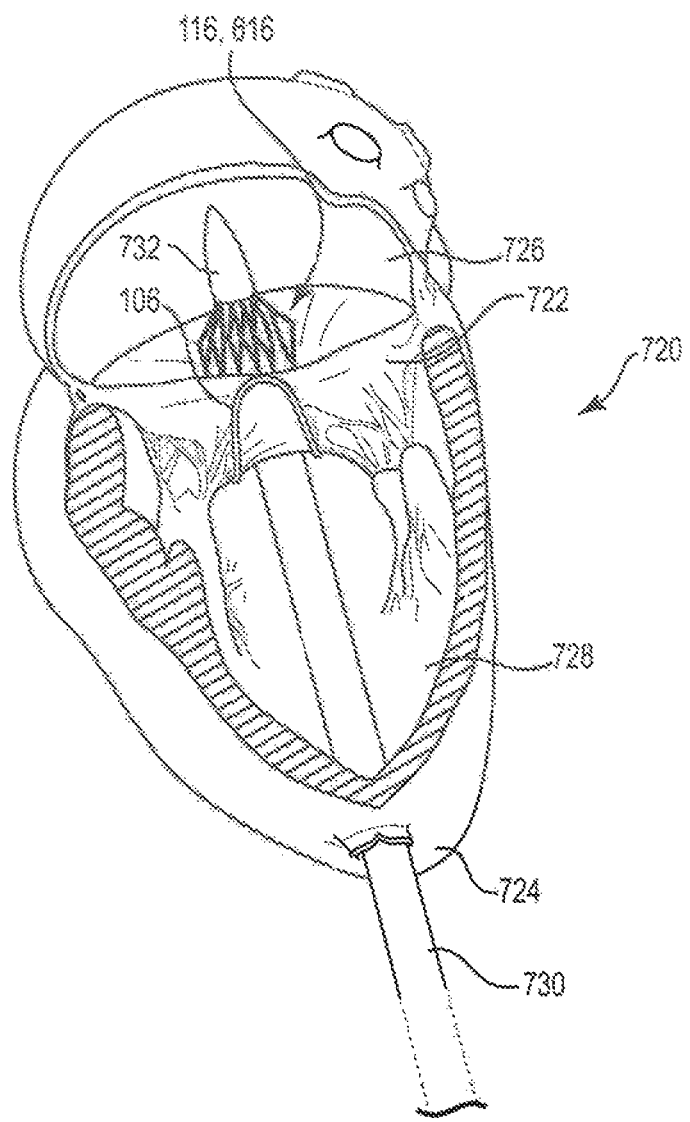
Figure 7E:
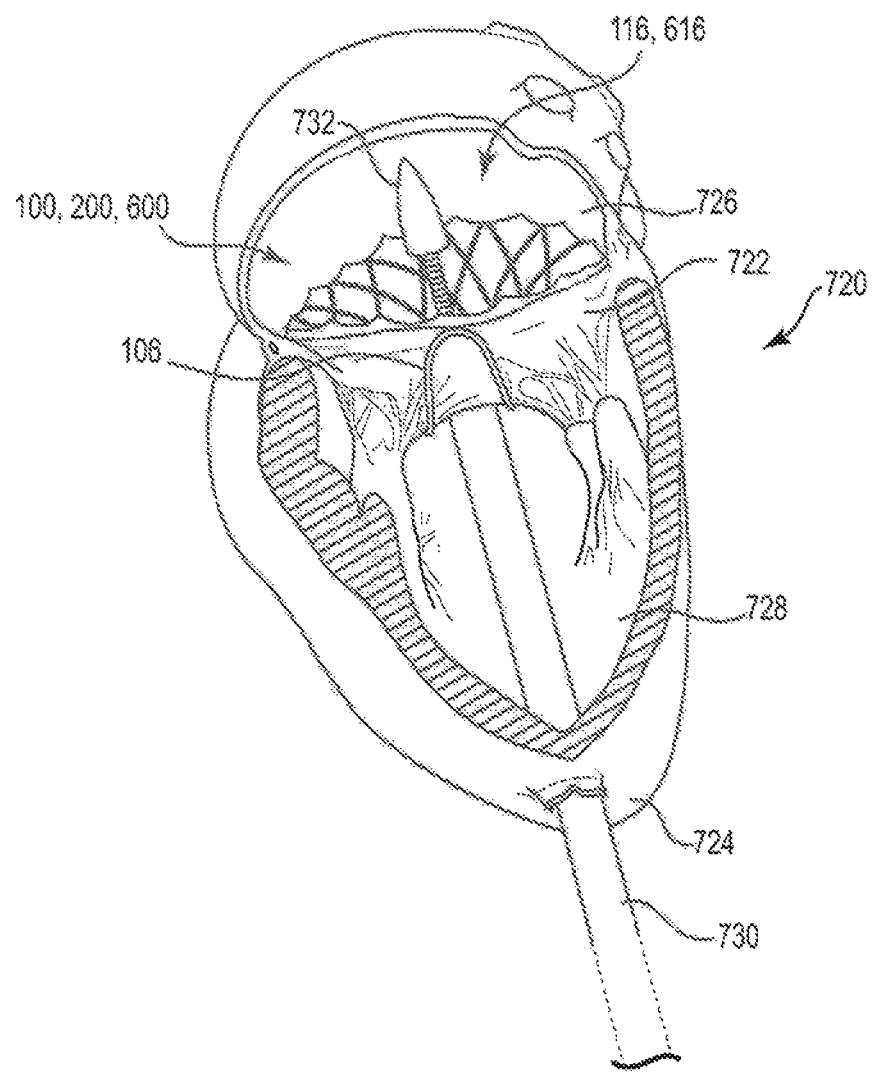
Figure 7F:
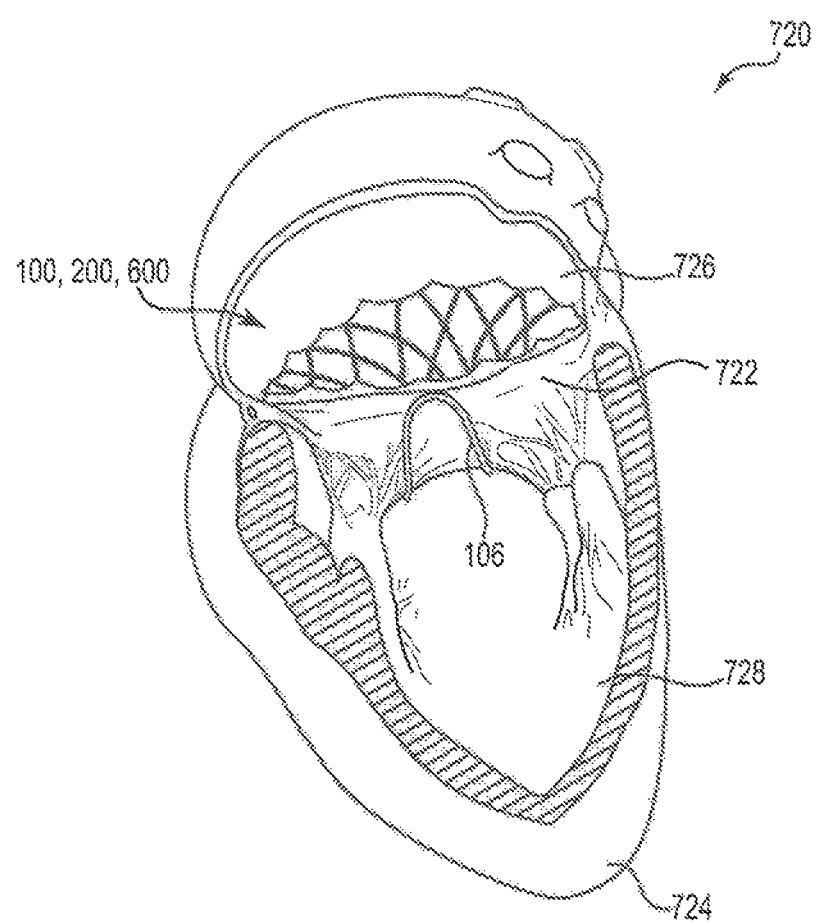

FIGS. 7A-7F depict a method of implanting a mitral valve prosthesis (e.g., prosthesis 100A, 100B, 200, 600A, or 600B) through a transapical procedure. As shown in FIG. 7A, a trocar (or overtube) 730 is inserted into the left ventricle 728 through an incision created in the apex 724 of a patient's heart 720. A dilator 732 is used to aid in the insertion of trocar 730. In this transapical approach, the native mitral valve 722 is approached from the downstream relative to the blood flow. In FIG. 7B, trocar 730 is retracted sufficiently to release the self-expanding engagement arms 106 of the mitral valve prosthesis. Dilator 732 is preferable presented between valve leaflets 722. Trocar 730 can be rotated and adjusted as necessary to properly align the valve prosthesis. In FIG. 7C, trocar 730 and the valve prosthesis is advanced forward such that outer engagement arms 106 clamp the native mitral valve leaflets 722. As shown in FIG. 7D, dilator 732 is advanced into the left atrium to further expose inner support structure 102 (or 602), and more specifically to begin disengaging proximal section 116 (or 616) from dilator 732. FIG. 7E shows proximal section 116 (or 616) released from dilator 732, and expanded to press against the interior wall for native mitral valve 722. In FIG. 7F, trocar 730 is withdrawn from heart 720 and the incision in apex 724 is closed.

Figure 8A:
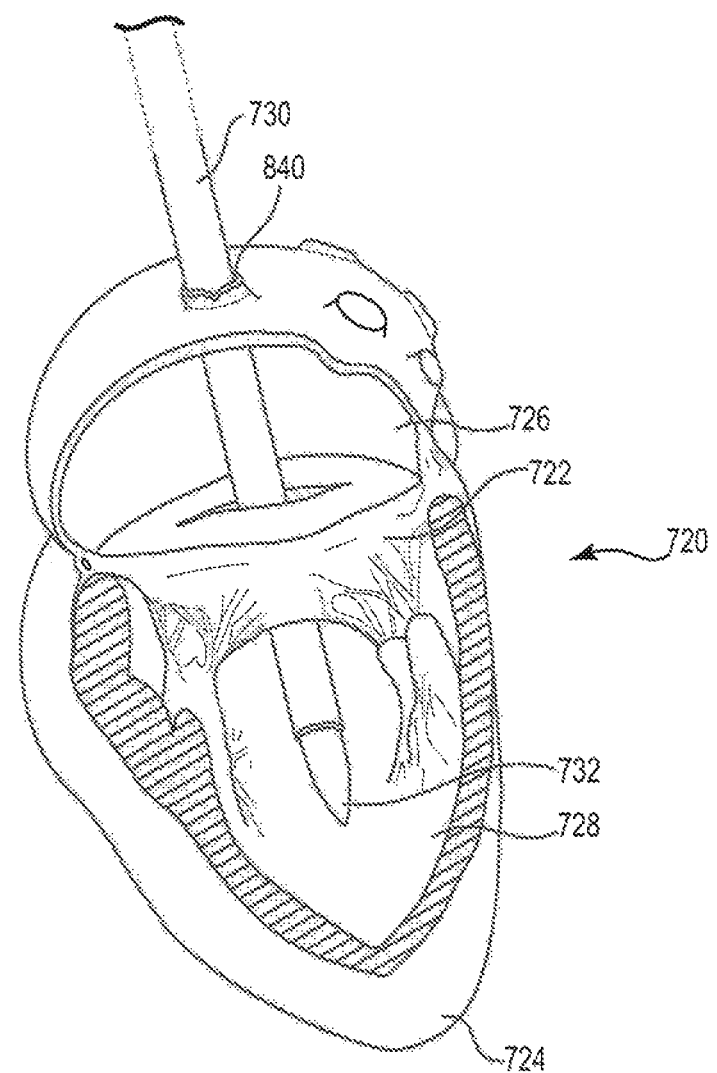
FIGS. 8A-8F depict a method of implanting a mitral valve prosthesis transatrially.
Figure 8B:
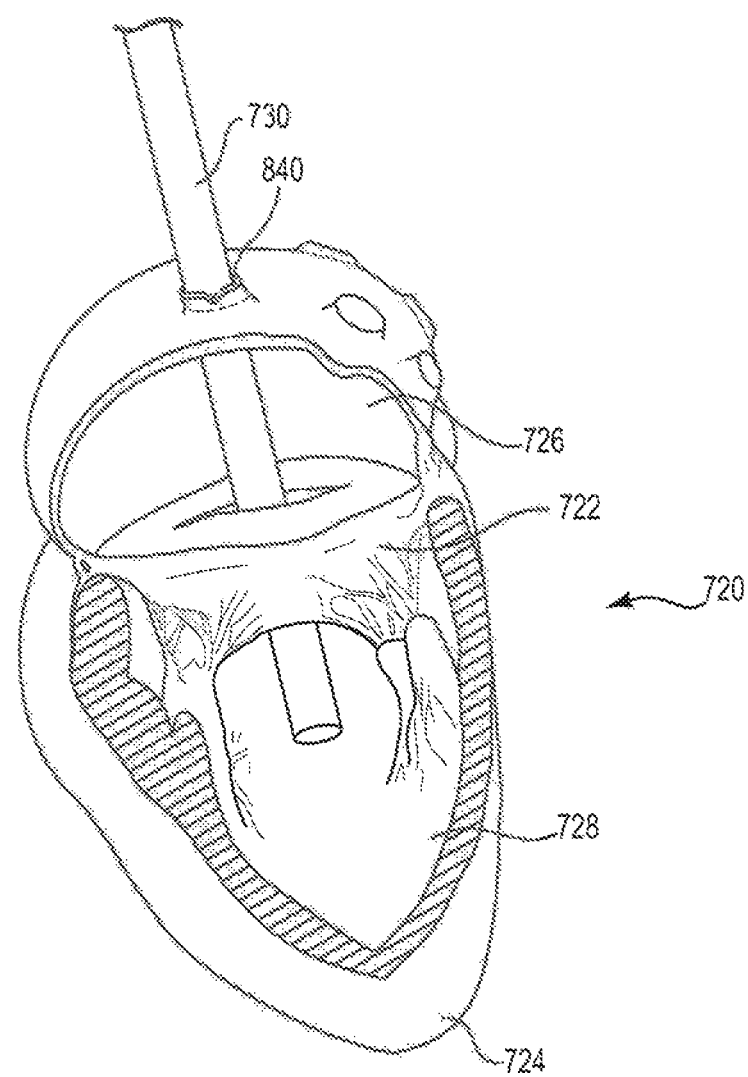
Figure 8C:
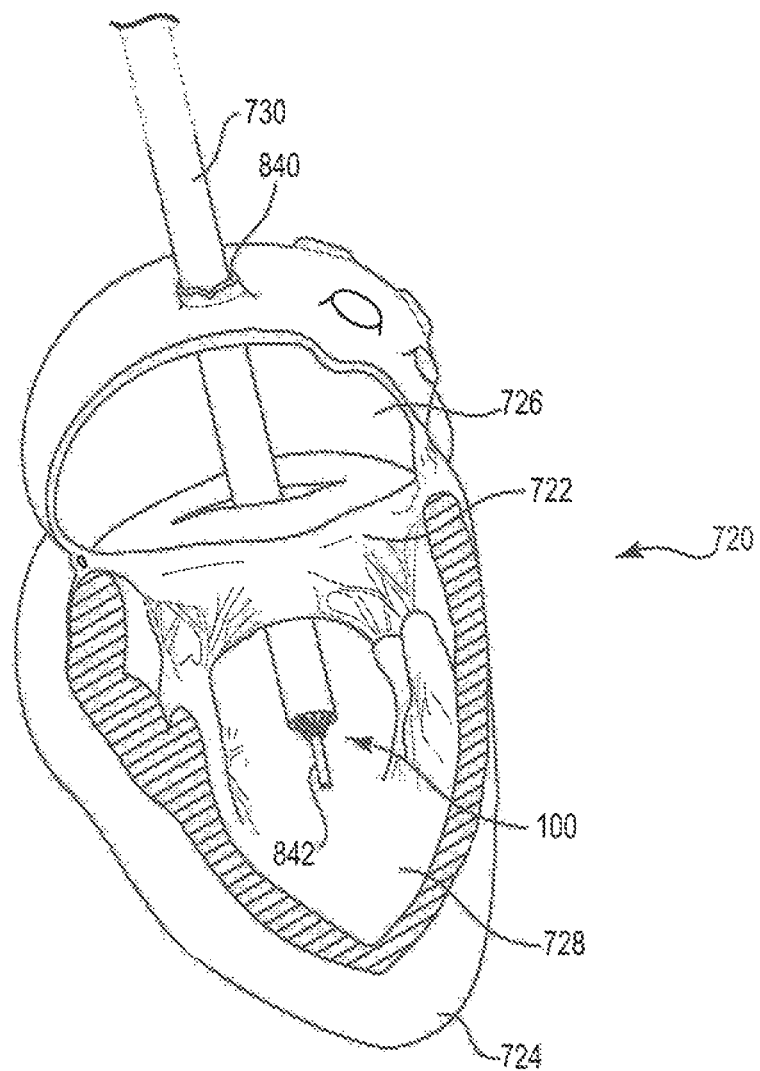
Figure 8D:
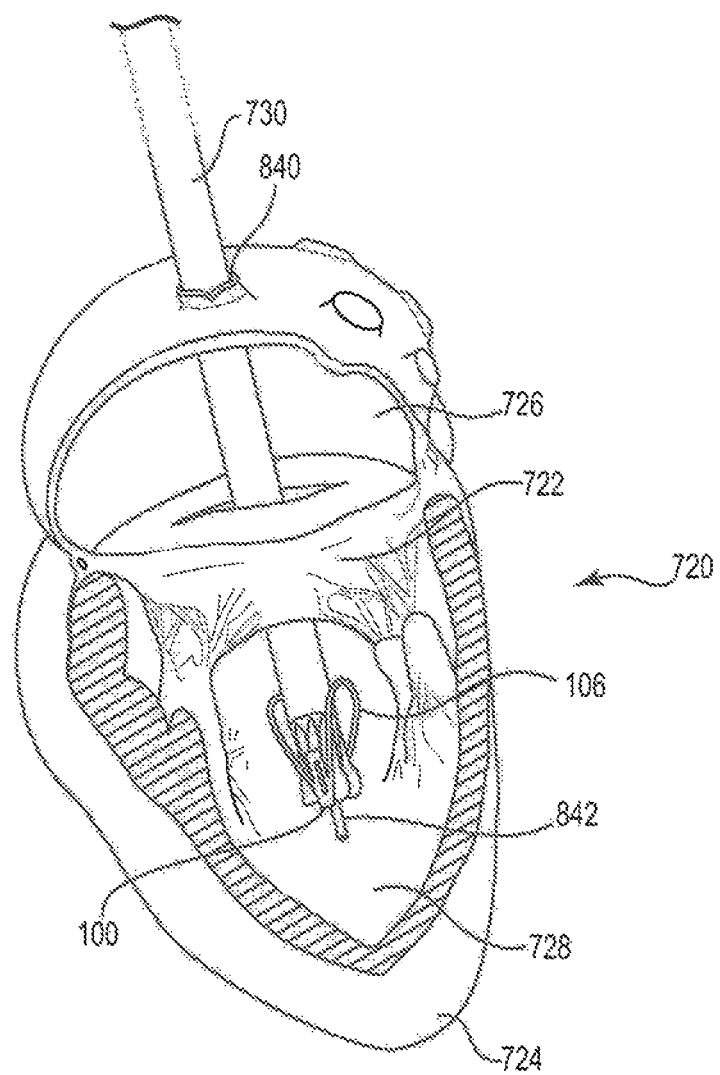
Figure 8E:
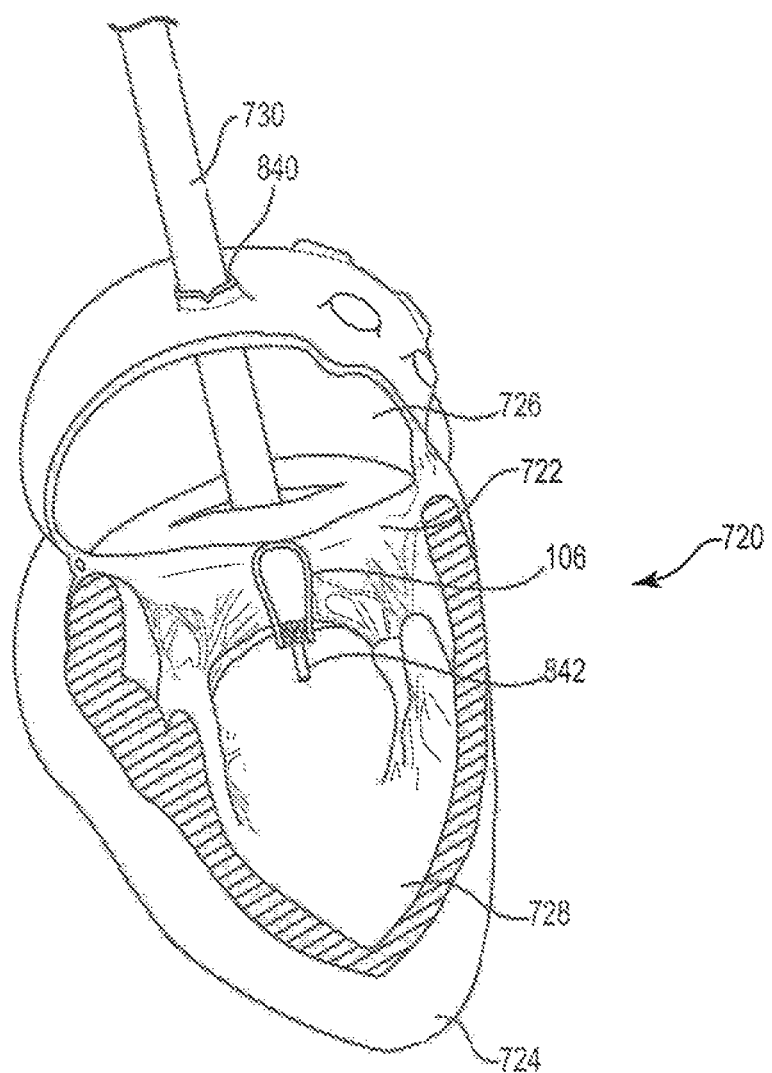
Figure 8F:
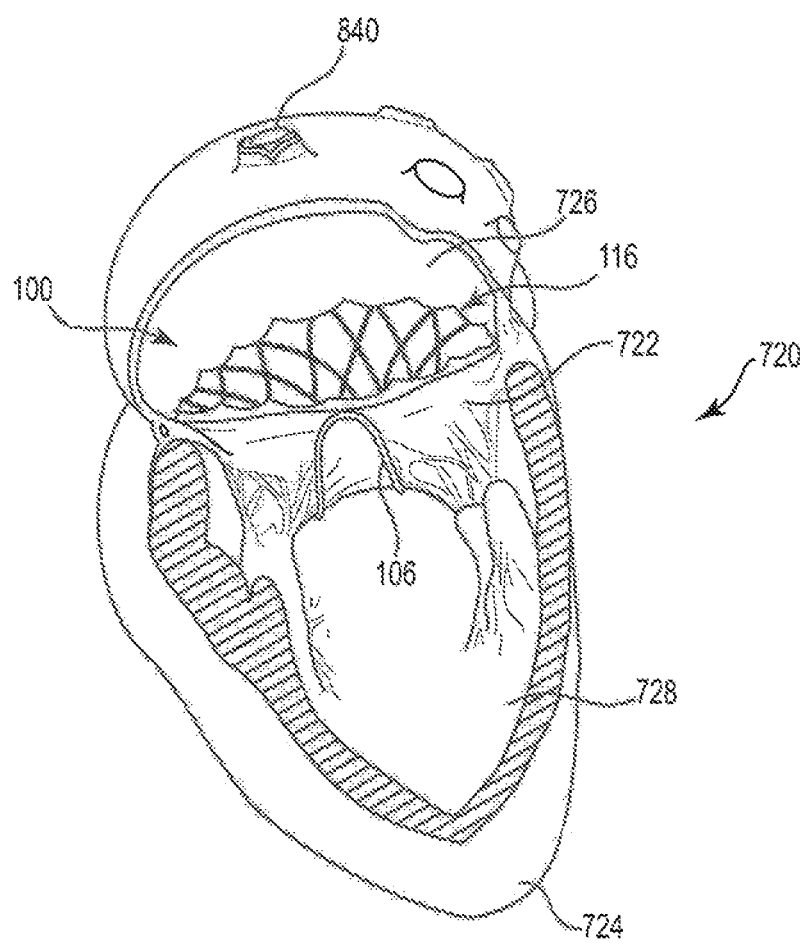

FIGS. 8A-8F depict a method of implanting a mitral valve prosthesis (e.g., prosthesis 100A, 100B, 200, 600A, or 600B) through a transatrial procedure. As shown in FIG. 8A, dilator 732 and trocar 730 are inserted through an incision 840 made in the wall of the left atrium of heart 720. Dilator 732 and trocar 730 are advanced through the native mitral valve 722 and into the left ventricle of heart 720. In FIG. 8B, dilator 732 is withdrawn from trocar 732. In FIG. 8C, a guide wire 842 is advanced through trocar 730 to the point where the mitral valve prosthesis 100A (or 100B, or 200, or 600A, or 600B) comes to the end of trocar 730. As shown in FIG. 8D, mitral valve prosthesis 100A is advanced sufficiently to release the self-expanding engagement arms 106 from trocar 730. Trocar 730 can be rotated and adjusted as necessary to properly align the valve prosthesis. In FIG. 8E, trocar 730 is withdrawn slightly so as to clamp engagement arms 106 on the outside of native valve leaflets 722. FIG. 8F shows trocar 730 completely withdrawn from heart 720 such that mitral valve prosthesis 100A (or 100B, or 200, or 600A, or 600B) self-expands into position and assumes the function of native mitral valve 722.

In an alternative embodiment, a mitral valve prosthesis (e.g., prosthesis 100A, 100B, 200, 600A, or 600B) may be implanted transeptally. In such embodiment, the prosthesis is snaked through the femoral vein, into the right atrium. An incision is made in the septum of the heart to provide access to the left atrium. The prosthesis is then advanced through the incision in the septum and is implanted through a technique similar to the one outlined with regard to FIGS. 8C-8F. Such a method would include: making an incision in a femoral vein; inserting a trocar through the incision in the femoral vein and advancing the trocar into the right atrium of the heart; making an incision in the septum of the heart; advancing the trocar through the incision in the septum of the heart and into the left atrium; advancing a mitral valve prosthesis through the trocar and into the left atrium of the heart; advancing the trocar past the native mitral valve and into the left ventricle of the heart; releasing the engagement arms from the trocar; retracting the trocar such that the engagement arms sit on the outer surface of the native mitral valve leaflets; releasing the inner support structure from the trocar, closing the incision in the septum; and withdrawing the trocar from the heart.

FIG. 9 shows a perspective view of mitral valve prosthesis 100A having engagement arms 106 clamping onto native mitral valve leaflets 722. The commissure posts 108 of prosthesis 100A sit on lop of native valve leaflets 722 and are in line with the prosthetic valve leaflets 118. As such the commissure posts 108 avoid interference with the LVOT and/or aortic valve.

Figure 10B:
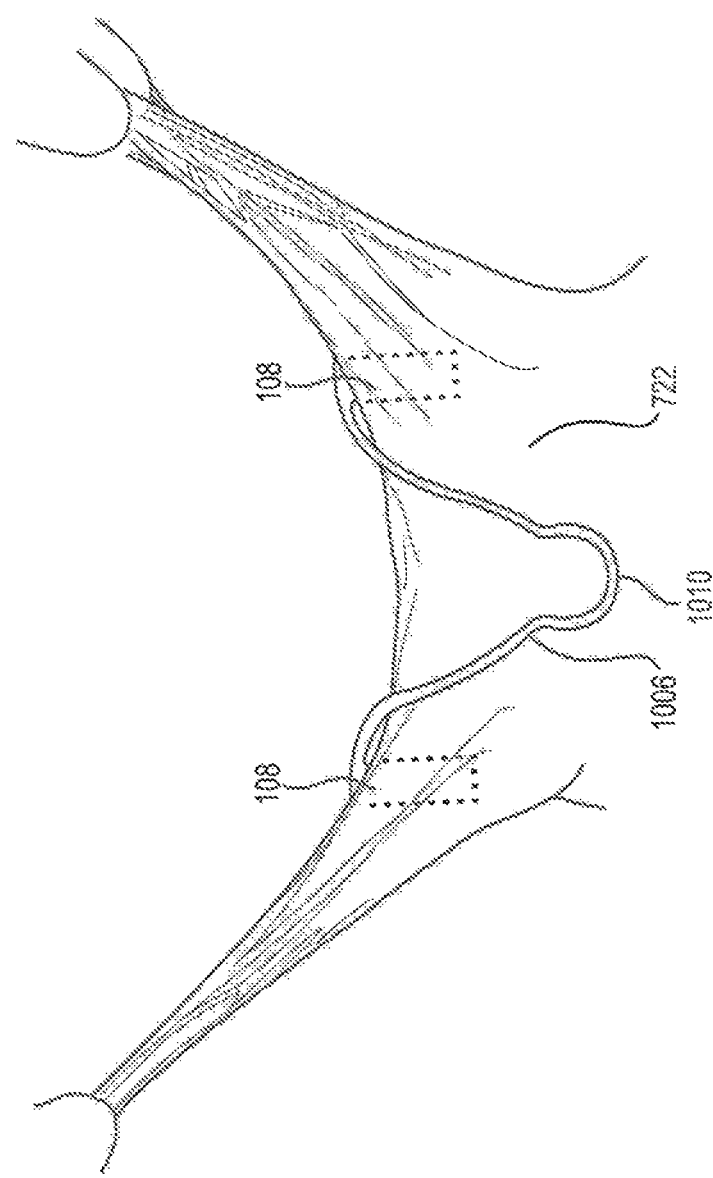
Figure 10D:
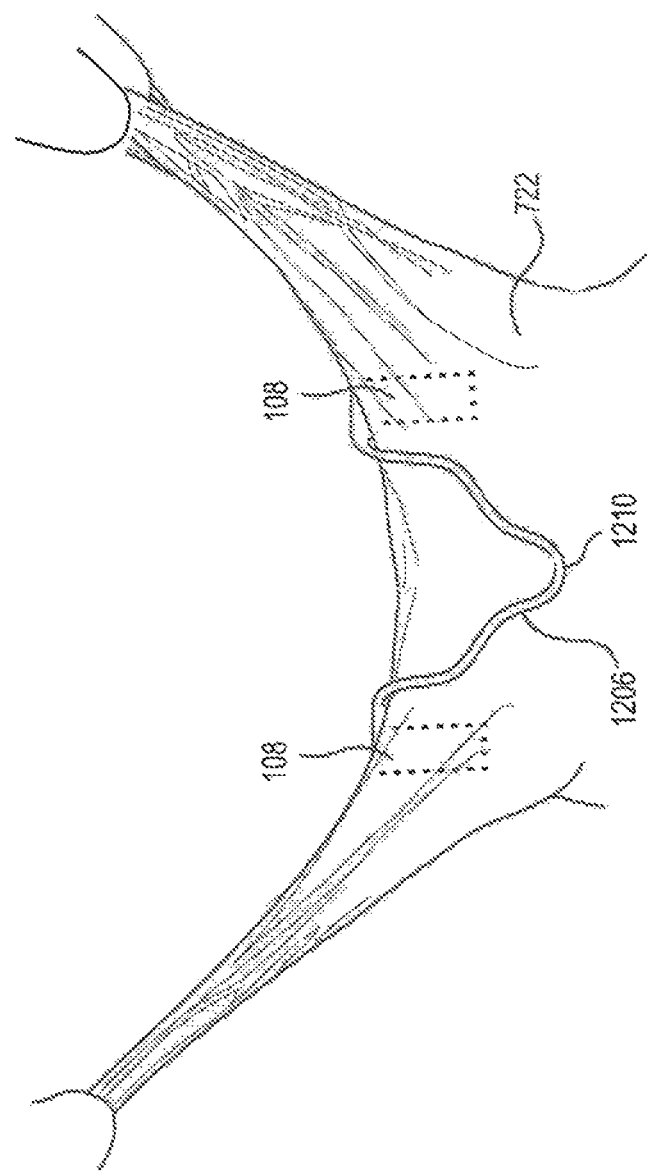

FIGS. 10A-10D show alternative embodiments for engagement arms 106, 1006, 1106, and 1206. In FIG. 10A, engagement arm 106 forms a U-shaped trough 110. In FIG. 10B, engagement arm 1006 forms a circular-shaped trough 1010. In FIG. 10C, engagement arm 1106 forms a bulging flask-shaped trough 1110. In FIG. 10D, engagement arm 1206 forms an undulating, bottle-nipple shaped trough 1210. In alternative embodiments (not shown), the engagement anus may be shaped to include two or more parallel arches.

Figure 11A:
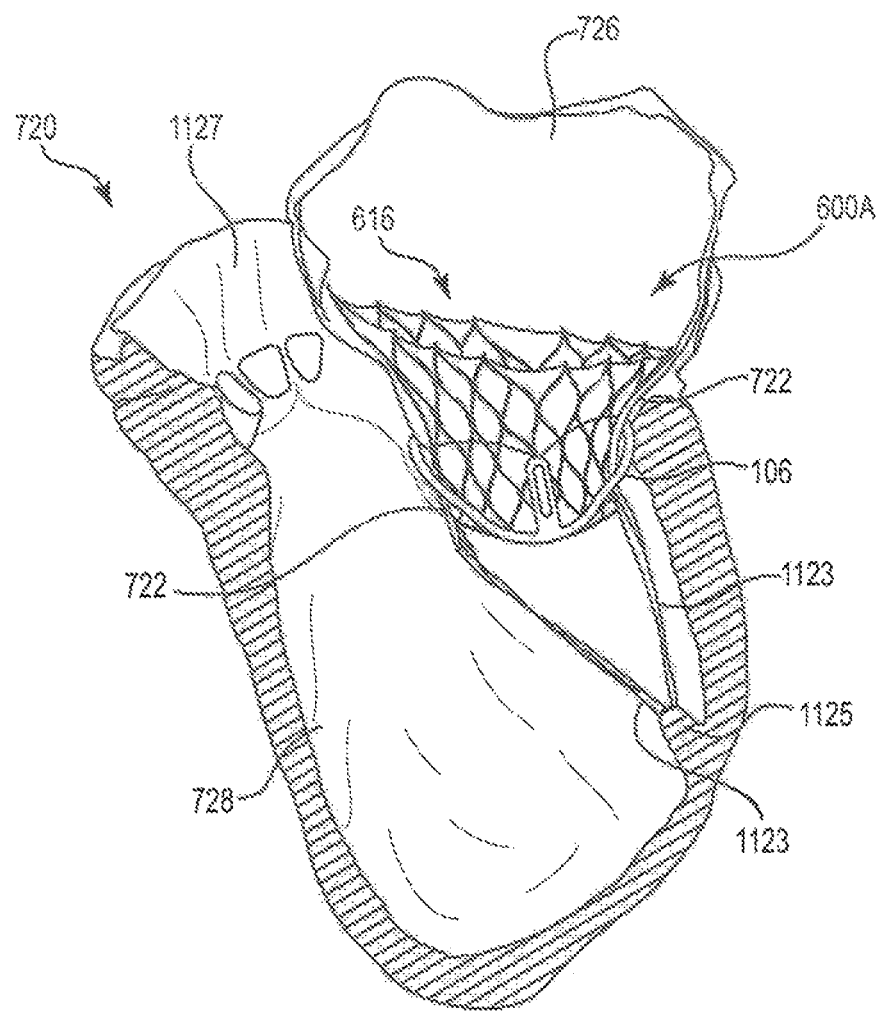
FIG. 11A is a saggital cut through a human heart depicting the implanted mitral valve prosthesis of FIG. 6.

FIG. 11A is a saggital cut through a human heart 720 depicting the implanted mitral valve prosthesis 600A of FIG. 6. The mitral cords 1123 connect native mitral valve 722 to the papillary muscles 1125. Engagement arms 106 wrap around and lock into native mitral valve 722. As shown in FIG. 11A, proximal section 616 has a non-circular, asymmetric shape to accommodate the anterior horn of atrium 726, which is associated anatomically with the position of aortic valve 1127. The shape of proximal section 616 ensures axial fixation, prevents outflow obstruction, and seals prosthesis 600A against the wall of left atrium 726.

Figure 11B:
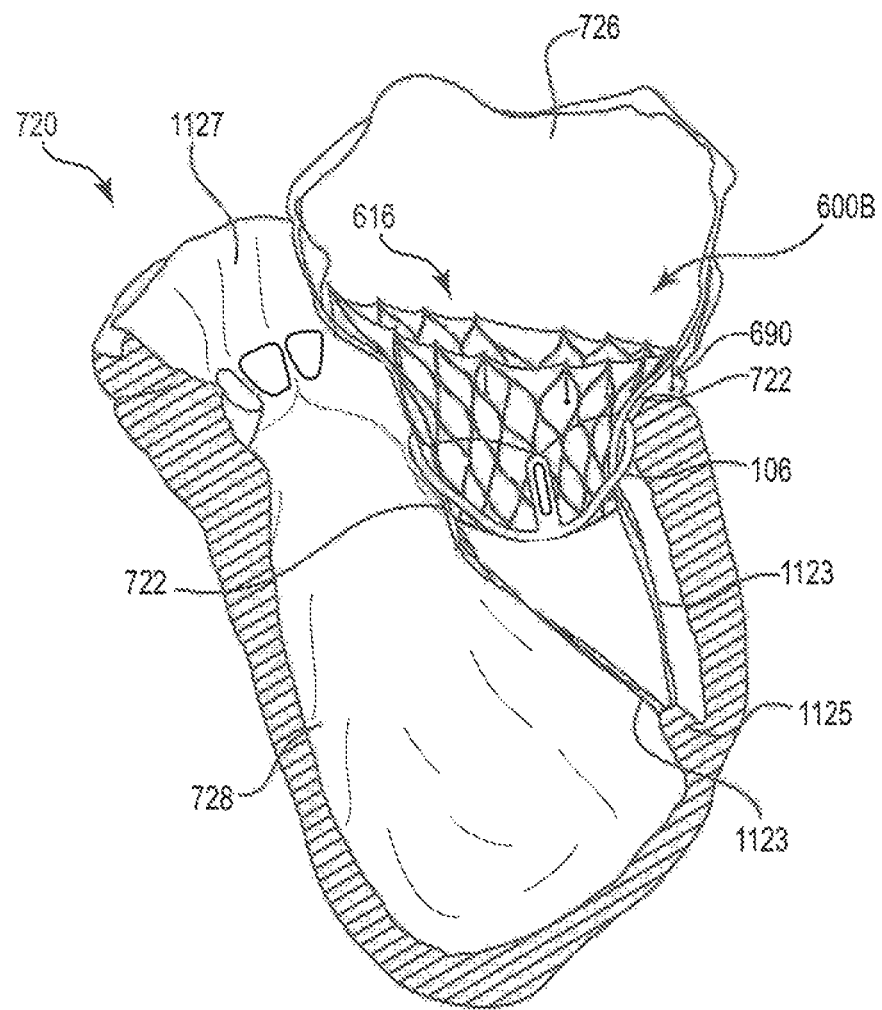
FIG. 11B is a saggital cut through a human heart depicting an implanted alternative embodiment to the mitral valve prosthesis of FIG. 6.

FIG. 11B is a saggital cut through a human heart 720 depicting an implanted mitral valve prosthesis 600B. The mitral cords 1123 connect native mitral valve 722 to the papillary muscles 1125. Engagement arms 106 wrap around and lock into native mitral valve 722. As shown in FIG. 11B, proximal section 616 has a non-circular, asymmetric shape to accommodate the anterior horn of atrium 726, which is associated anatomically with the position of aortic valve 1127. The shape of proximal section 616 ensures axial fixation, prevails outflow obstruction, and seals prosthesis 600B against the wall of left atrium 726. Further, barbs 690 penetrate to the mitral annulus and serve as a locking mechanism, together with engagement arms 106, to prevent migration of prosthesis 600D into left ventricle 728.

The foregoing description has been presented for purposes of illustration and enablement, and is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A heart valve prosthesis comprising:
   a frame comprising an inner support structure including an expandable inflow section having an asymmetrical shape and an outer support structure coupled to the inner support structure, the outer support structure including a first commissure post and first and second engagement arms, wherein the first commissure post is parallel to a longitudinal axis of the inner support structure and wherein a first end of the first engagement arm is attached to the first commissure post and a first end of the second engagement arm is attached to the first commissure post; and a valve structure attached to the frame within an interior area of the inner support structure.

2. The prosthesis of claim 1, wherein the inflow section comprises a plurality of cells.

3. The prosthesis of claim 1, wherein the frame further comprises an expandable outflow section.

4. The prosthesis of claim 3, wherein the outflow section comprises a plurality of cells.

5. The prosthesis of claim 3, wherein the outflow section has a circular cross-section.

6. The prosthesis of claim 3, wherein the outflow section is configured to expand within and support against a native valve annulus.

7. The prosthesis of claim 3, wherein the inflow section is flared outward from the outflow section.

8. The prosthesis of claim 1, wherein one of the engagement arms is self-expanding.

9. The prosthesis of claim 1, wherein the frame further comprises a second commissure post parallel to the longitudinal axis of the inner support structure.

10. The prosthesis of claim 9, wherein a second end of the first engagement arm is attached to the second commissure post and a second end of the second engagement arm is attached to the second commissure post.

11. The prosthesis of claim 1, wherein the inflow section is configured to expand within and support against an atrium.

12. The prosthesis of claim 1, wherein the frame further comprises fixation barbs attached to the inflow section.

13. A heart valve prosthesis comprising:

a frame comprising:

an inner support structure including an expandable inflow section having an asymmetrical shape and an expandable outflow section; and an outer support structure coupled to the inner support structure, the outer support structure including first and second commissure posts and first and second engagement arms, wherein the first and second commissure posts are parallel to a longitudinal axis of the inner support structure, wherein a first end of the first engagement arm is attached to the first commissure post and a first end of the second engagement arm is attached to the first commissure post, wherein a second end of the first engagement arm is attached to the second commissure post and a second end of the second engagement arm is attached to the second commissure post; and a valve structure attached to the frame within an interior area of the inner support structure.

* * * * *